(12) United States Patent
Kawagishi et al.

(10) Patent No.: US 6,506,158 B2
(45) Date of Patent: Jan. 14, 2003

(54) ULTRASONIC DIAGNOSIS APPARATUS

(75) Inventors: Tetsuya Kawagishi, Kuroiso (JP); Ryoichi Kanda, Otawara (JP); Yoshitaka Mine, Nasu-gun (JP)

(73) Assignee: Kabushiki Kaisha Toshiba, Kawasaki (JP)

( * ) Notice: Subject to any disclaimer, the term of this patent is extended or adjusted under 35 U.S.C. 154(b) by 5 days.

(21) Appl. No.: 09/827,926

(22) Filed: Apr. 9, 2001

(65) Prior Publication Data

US 2001/0034485 A1 Oct. 25, 2001

(30) Foreign Application Priority Data

Apr. 10, 2000 (JP) .......................... 2000-108097

(51) Int. Cl.$^7$ ............................... A61B 8/00
(52) U.S. Cl. ..................... 600/443; 600/458
(58) Field of Search ............... 600/437, 440–447, 600/458; 73/625, 626; 367/7, 11, 138

(56) References Cited

U.S. PATENT DOCUMENTS

| | | |
|---|---|---|
| 5,632,277 A | 5/1997 | Chapman et al. |
| 5,706,819 A | 1/1998 | Hwang et al. |
| 5,902,243 A * | 5/1999 | Holley et al. ............... 600/443 |
| 5,951,478 A | 9/1999 | Hwang et al. |
| 6,095,977 A * | 8/2000 | Hall et al. .................. 600/443 |

OTHER PUBLICATIONS

Iwao Abiru, et al., "Nonlinear Propagation of a Pulsed Ultrasound," Singaku–gihou, US89–23, pp. 53–60.

* cited by examiner

Primary Examiner—Marvin M. Lateef
Assistant Examiner—Ali M. Imam
(74) Attorney, Agent, or Firm—Oblon, Spivak, McClelland, Maier & Neustadt, P.C.

(57) ABSTRACT

An ultrasonic diagnosis apparatus includes an ultrasonic probe. A transmitter supplies a transmission pulse to the ultrasonic probe to repeatedly transmit an ultrasonic wave to each of a plurality of scanning lines. A receiver receives echoes of the ultrasonic waves through the ultrasonic probe and obtaining a plurality of received signals for each of the plurality of scanning lines. A displacement estimating means estimates a relative change accompanying a tissue motion between received signals associated with each of scanning lines. A displacement correcting means corrects the received signals in accordance with the change detected by the displacement estimating means. A harmonic component extracting means extracts a harmonic component from the received signals corrected by the displacement correcting means. A display means generates an ultrasonic image on the basis of the harmonic component extracted by the harmonic component extracting means. A monitor displays the image generated by the display means.

24 Claims, 14 Drawing Sheets

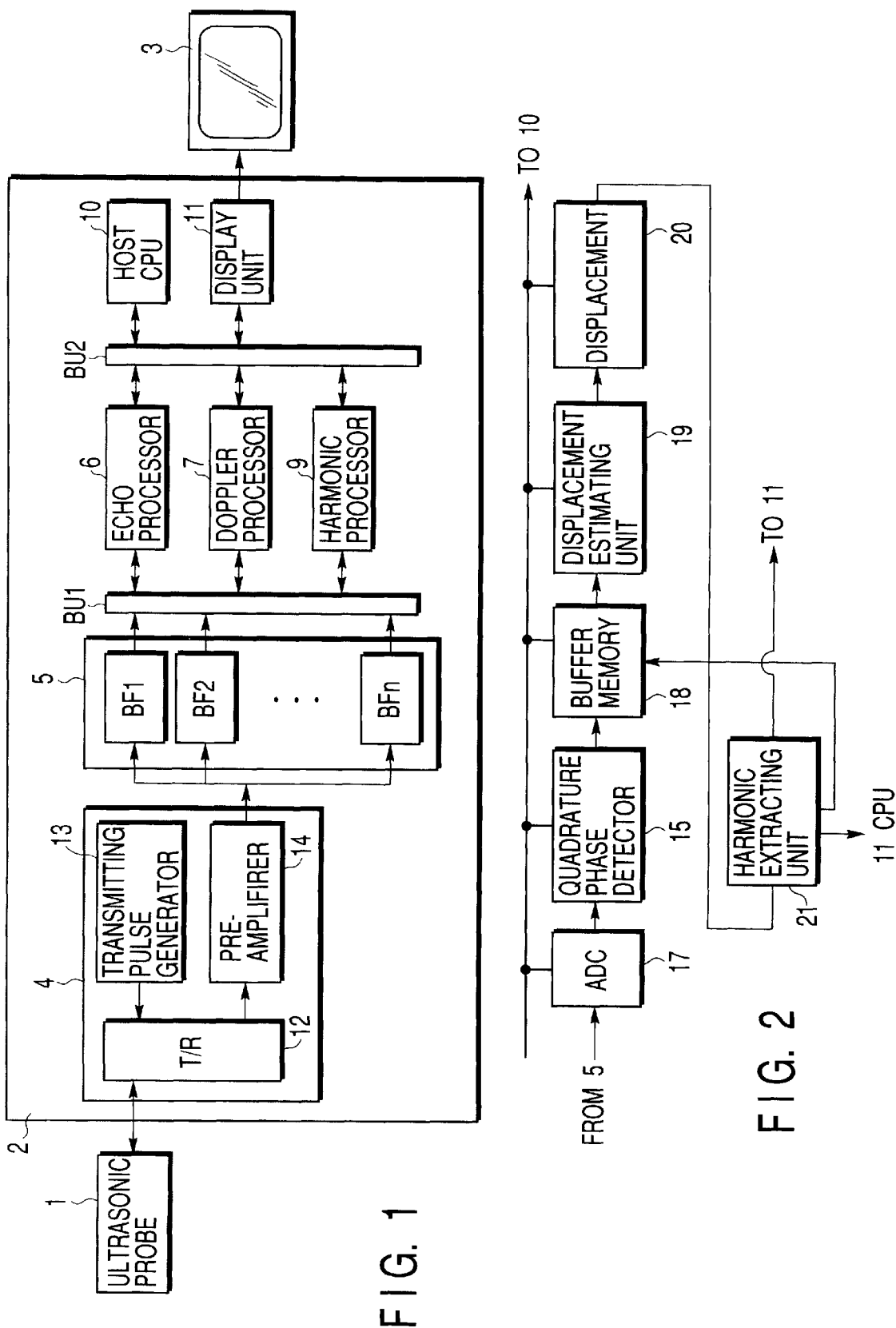

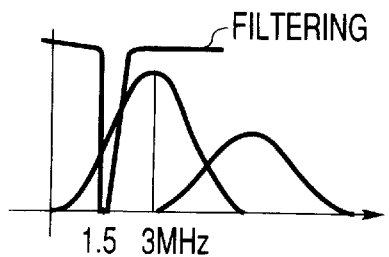
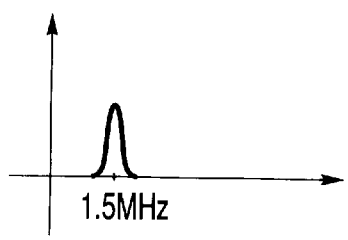
FIG. 9A    FIG. 9B
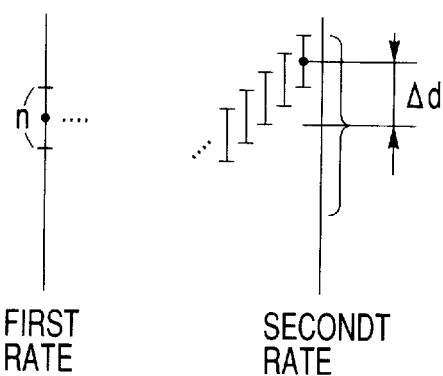
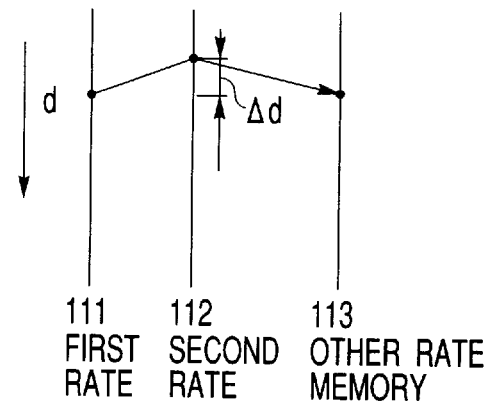
FIG. 10A  FIG. 10B    FIG. 11
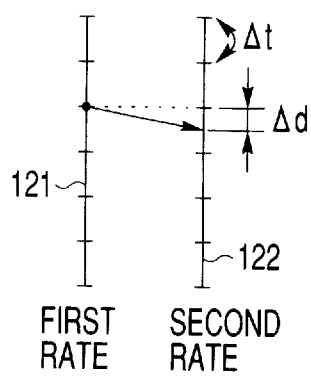
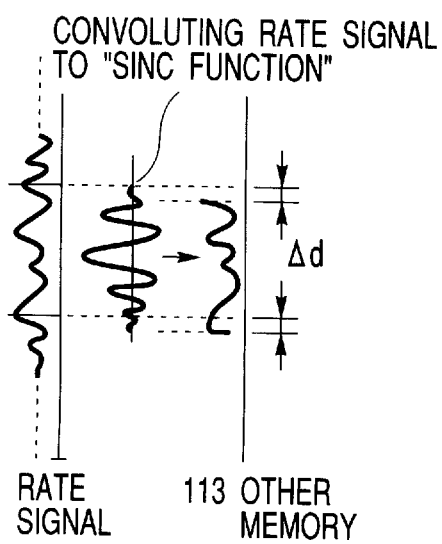
FIG. 12    FIG. 13

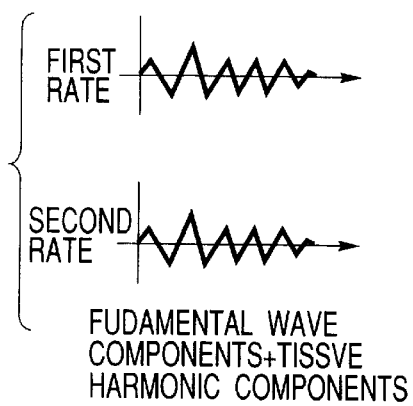
FIG. 20A  FUDAMENTAL WAVE COMPONENTS+TISSVE HARMONIC COMPONENTS
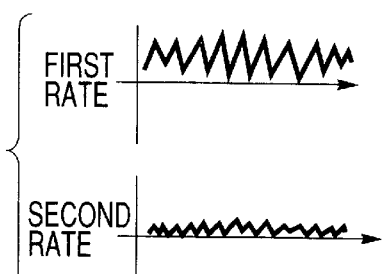
FIG. 20B  BUBBLE
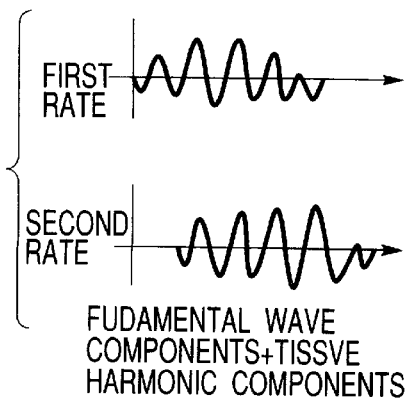
FIG. 20C  FUDAMENTAL WAVE COMPONENTS+TISSVE HARMONIC COMPONENTS
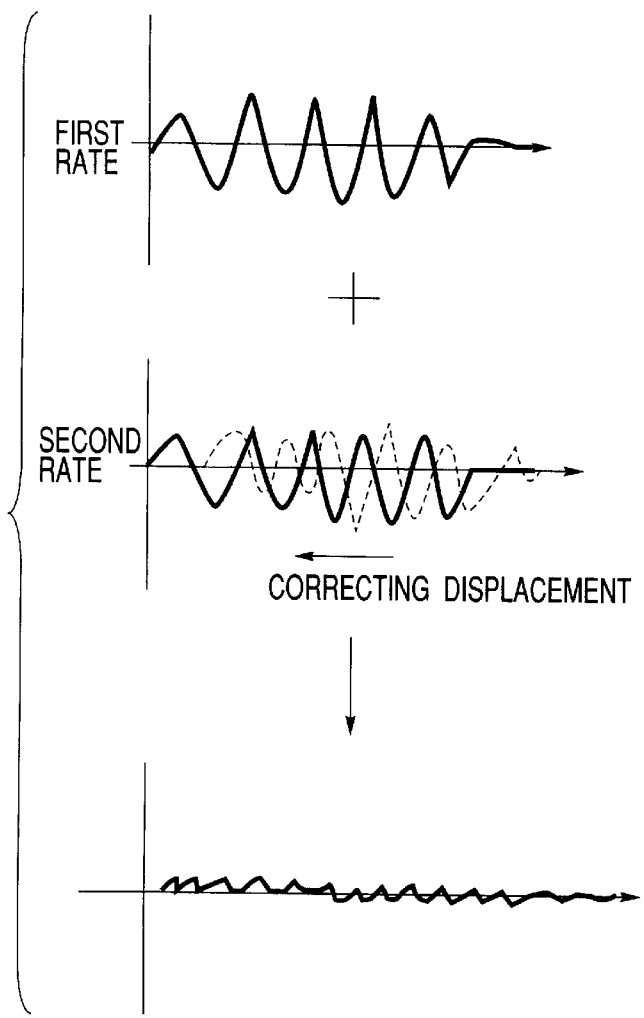
FIG. 21

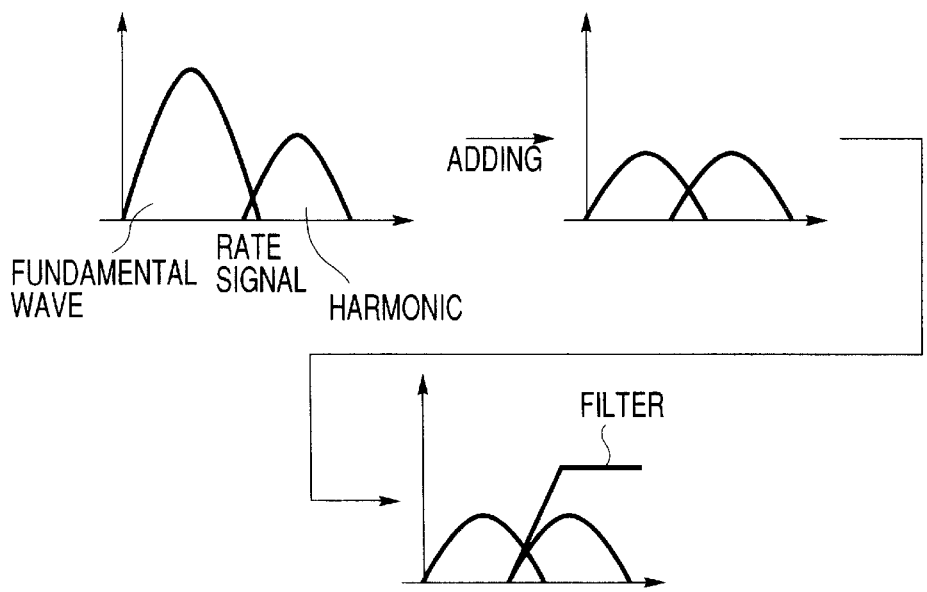
F I G. 26
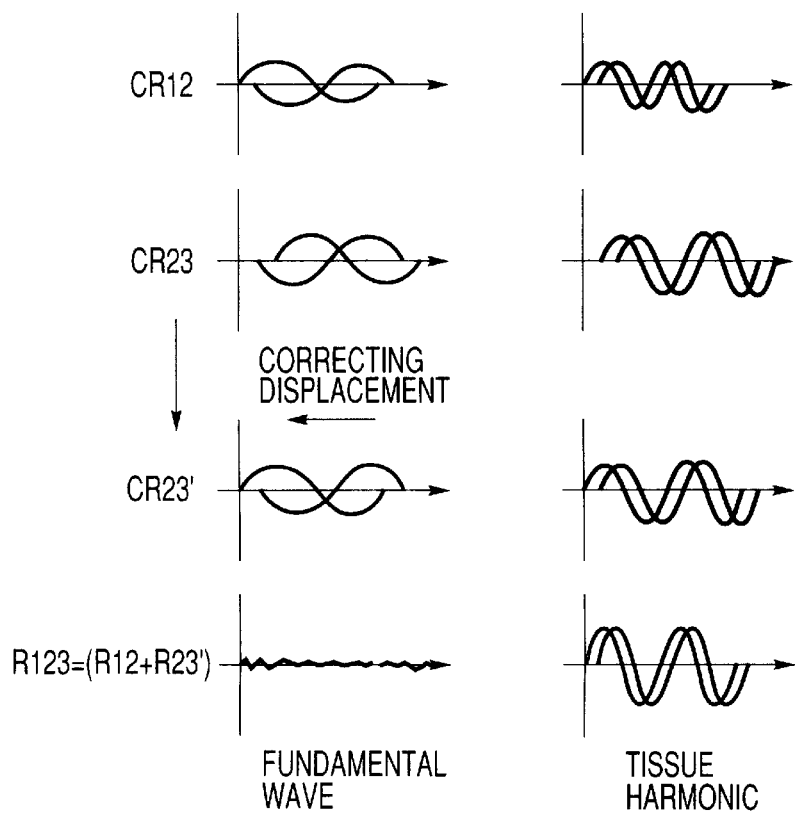
F I G. 27A  F I G. 27B

CH123=CR12(t)-CR23(t+T)

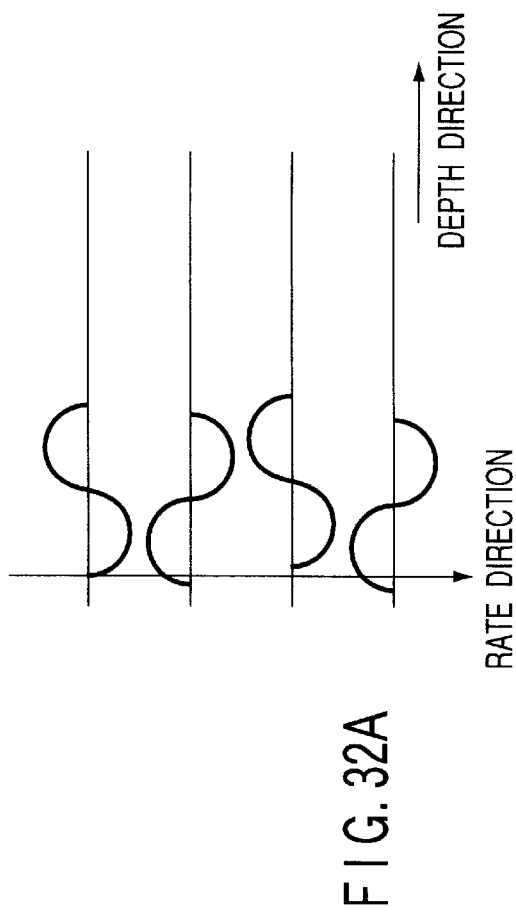
FIG. 32A
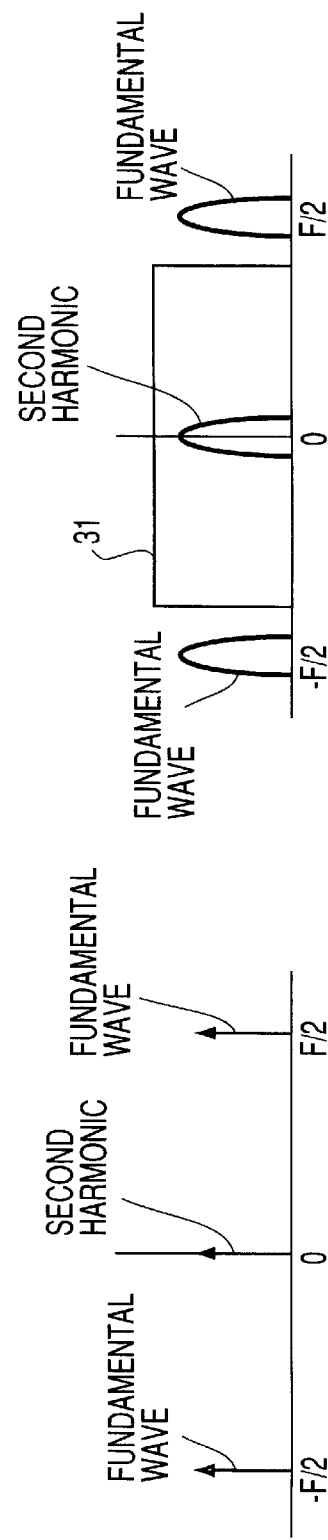
FIG. 32B
FIG. 32C

ULTRASONIC DIAGNOSIS APPARATUS

CROSS-REFERENCE TO RELATED APPLICATIONS

This application is based upon and claims the benefit of priority from the prior Japanese Patent Application No. 2000-108097, filed Apr. 10, 2000, the entire contents of which are incorporated herein by reference.

BACKGROUND OF THE INVENTION

The present invention relates to an ultrasonic diagnosis apparatus for extracting harmonic components generated by nonlinear propagation of the living tissue and the nonlinear response of a contrast medium (microbubbles) from a received signal, and generating an ultrasonic image on the basis of the harmonic components.

Imaging based on harmonic components can substantially narrow a beam as compared with imaging based on fundamental wave components that spread from the center frequency of a transmission ultrasonic wave, and hence can realize high resolution. In addition, a certain sound pressure is required to generate harmonic components, imaging based on harmonic components can reduce side lobes. As a method of imaging harmonic components originating from the tissue, THI (Tissue Harmonic Imaging) is available.

A filter method is a typical method of extracting nonlinear components from a received signal. As a method of extracting harmonic components in a wider band, a pulse inversion method is available, in which two ultrasonic pulses having opposite polarities are transmitted at two rates, and signals received at the respective rates are added to cancel out a fundamental wave component, thereby extracting harmonic components as disclosed in Iwao Abiru and Tomoo Kamakura, "Nonlinear Propagation of Ultrasonic Pulses" (Technical Report of IEICE, US89-23, p. 53). This method uses the phenomenon that harmonic components are generated in proportion to the square of a fundamental wave. More specifically, since the phases of fundamental wave components maintain the phase of a transmission ultrasonic wave, the first rate fundamental wave component appears in opposite polarity to the second rate fundamental wave component. Therefore, the fundamental wave components cancel out each other. On the other hand, harmonic components are generated in proportion to the square of a fundamental wave, and hence the first rate harmonic component and second rate harmonic component appear in the same polarity. Therefore, the harmonic components are amplified.

The fundamental wave elimination characteristic of the above pulse inversion method is based on the premise that the tissue serving as a propagation medium is still. If, therefore, a moving organ such as the heart is imaged by the pulse inversion method, the received signal waveform and relative positions (depths) of the received signal changes between the two rates in accordance with the motion of the organ. As a consequence, fundamental wave components are left to cause motion artifacts on an image.

BRIEF SUMMARY OF THE INVENTION

It is an object of the present invention to eliminate motion artifacts due to the motion of tissue such as the heart, in particular, in an ultrasonic diagnosis apparatus for repeatedly transmitting an ultrasonic wave, extracting harmonic components from a plurality of received signals obtained by the transmission of the ultrasonic wave, and generating images on the basis of the harmonic components.

An ultrasonic diagnosis apparatus includes an ultrasonic probe, a transmitter configured to supply a transmission pulse to the ultrasonic probe to repeatedly transmit an ultrasonic wave to each of a plurality of scanning lines, and a receiver configured to receive echoes of the ultrasonic waves through the ultrasonic probe and obtaining a plurality of received signals for each of the plurality of scanning lines. A displacement estimating means estimates a relative change accompanying a tissue motion between a plurality of received signals associated with each of the plurality of scanning lines. A displacement correcting means corrects the plurality of received signals in accordance with the change detected by the displacement estimating means. A harmonic component extracting means extracts a harmonic component from the plurality of received signals corrected by the displacement correcting means. A display means generates an ultrasonic image on the basis of the harmonic component extracted by the harmonic component extracting means. A monitor displays the image generated by the display means.

According to the present invention, harmonic components can be extracted in a broad band even from moving organs such as the heart, in particular, and high-quality images unique to harmonic images can be provided for clinical sites.

Additional objects and advantages of the invention will be set forth in the description which follows, and in part will be obvious from the description, or may be learned by practice of the invention. The objects and advantages of the invention may be realized and obtained by means of the instrumentalities and combinations particularly pointed out hereinafter.

BRIEF DESCRIPTION OF THE SEVERAL VIEWS OF THE DRAWING

The accompanying drawings, which are incorporated in and constitute a part of the specification, illustrate presently preferred embodiments of the invention, and together with the general description given above and the detailed description of the preferred embodiments given below, serve to explain the principles of the invention.

FIG. 1 is a block diagram showing the arrangement of an ultrasonic diagnosis apparatus according to a preferred embodiment of the present invention;

FIG. 2 is a block diagram showing the arrangement of a harmonic processor in FIG. 1;

FIGS. 9A and 9B are graphs for a supplementary explanation of filtering processing for the extraction of low-frequency components in a narrow band which is performed before phase estimation in this embodiment;

FIGS. 10A and 10B are views showing cross-correction between two rates in this embodiment;

FIG. 11 is a view for a supplementary explanation of processing of recording a complex value corresponding to displacement correction in an other rate memory in this embodiment;

FIG. 12 is a view for a supplementary explanation of processing of recording a complex value when an estimated displacement is smaller than a sampling interval;

FIG. 13 is a view for a supplementary explanation of processing of realizing correction of a displacement smaller than a sampling interval by using an interpolation method in this embodiment;

FIGS. 20A to 20C are graphs showing signal components based on rate differences in this embodiment;

FIG. 21 is a graph showing a rate difference after displacement correction in this embodiment;

FIG. 26 is a graph for a supplementary explanation of filtering processing for the elimination of harmonic components in this embodiment;

FIGS. 27A and 27B are graphs for a supplementary explanation of processing of performing displacement correction for addition signals and further adding them in this embodiment;

FIGS. 32A to 32C are graphs showing a plurality of rates in this embodiment.

DETAILED DESCRIPTION OF THE INVENTION

Figure 3A:
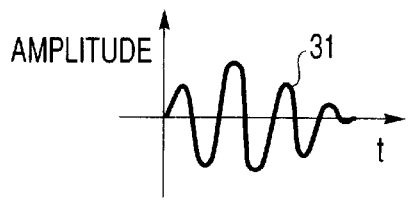
FIGS. 3A and 3B are graphs showing examples of two types of ultrasonic pulses which have opposite polarities and are transmitted in accordance with the pulse inversion method in this embodiment.

An ultrasonic diagnosis apparatus according to a preferred embodiment of the present invention will be described below with reference to the views of the accompanying drawing.

FIG. 1 shows an example of the arrangement of an ultrasonic diagnosis apparatus according to this embodiment. This ultrasonic diagnosis apparatus is comprised of an apparatus body 2 as a main component, an ultrasonic probe 1, and a monitor 3. In the FIG. 1, each processing of sections 5–11 is realized by a special purpose hardware or a software which can be carried out with a computer. In the apparatus body 2, a transmitting pulse generator 13 applies a pulse voltage to a transmitting/receiving circuit 12. The transmitting/receiving circuit 12 applies a driving voltage to the ultrasonic probe 1 having a plurality of vibrators arranged one- or two-dimensionally. The transmitting pulse generator 13 controls a transmission pulse voltage applied to a plurality of vibrators of the ultrasonic probe 1 to two- or three-dimensionally control the direction and convergence of an ultrasonic beam. This operation will be referred to as transmission beam forming hereinafter.

An ultrasonic signal applied from the ultrasonic probe 1 connected to the apparatus body 2 into the body and reflected by an acoustic impedance boundary in the body tissue or an ultrasonic signal backscattered by a small scatterer is received by the same ultrasonic probe 1. This received signal contains an echo from a harmonic component originating from the nonlinearity of vital propagation and an echo from a contrast medium. The received signal is sent to processors 6, 7, and 9 via a preamplifier 4 and reception delay circuit 5. The reception delay circuit 5 performs beam forming in receiving operation to control the directions and convergence of beams, and is comprised of a plurality of circuit sets BF1, BF2, . . . , BFn to form a plurality of beams and perform parallel, concurrent reception.

The echo processor 6 generates a two- or three-dimensional space distribution image corresponding to a signal amplitude intensity with a reference frequency after envelope detection. This image contains the two- or three-dimensional form information of an object to be examined. If a contrast medium is used for the object, the image contains form information and contrast medium information. The doppler processor 7 generates a two- or three-dimensional space distribution image of velocity, power, or variance by measuring a change in phase between received signals over time. This image contains blood flow rate information on the heart and its neighboring portion. The harmonic processor 9 extracts a fundamental wave harmonic component from a received signal. The signal processed by the respective processors is sent to a displaying unit 11 to be logarithmically compressed and scanned/converted. The resultant signal is displayed as an image on the monitor 3.

The above processors other than the harmonic processor 9 are commercially available products that have known arrangements and are based on known techniques. Since they are not directly relevant to the present invention, a detailed description thereof will be omitted.

The harmonic processor 9 that is relevant to the present invention will be described with reference to FIG. 2. The received signal that is beam-formed and output from the reception delay circuit 5 is converted into a digital signal by an ADC 17. This signal is subjected to quadrature phase detection in a quadrature phase detector 15 with the frequency of a fundamental wave. With this operation, a complex signal is obtained. This complex signal is stored in a buffer memory 18. A displacement estimating unit 19, displacement correcting unit 20, and harmonic extracting unit 21 extract harmonic components from a plurality of ultrasonic signals with respect to a plurality of scanning lines which are stored in the buffer memory 18. In actual signal processing, correction of an estimated displacement and signal processing for harmonic extraction may be simultaneously performed. The displacement correcting unit 20 and harmonic extracting unit 21 may therefore be integrated into one unit.

If a coded ultrasonic or pulse compression technique is to be used, quadrature phase detection is not always required. The quadrature phase detector 15 may be bypassed or a signal may be passed therethrough without any processing. If the apparatus is exclusively designed for this technique, the quadrature phase detector may be omitted.

(Signal Processing)

Figure 3B:
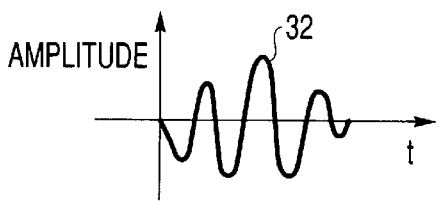

The principle of actual extraction of harmonic components by nonlinear propagation of tissue without any motion artifact with the above arrangement will be described in detail below by taking general two-rate ultrasonic pulse transmission as an example. An ultrasonic pulse 32 in FIG. 3B, as one of pulses based on two rates, has an opposite polarity to an ultrasonic pulse 31 in FIG. 3A. In other words, the two types of pulses are 180° out of phase (opposite phases). As described above, the two types of ultrasonic pulses 31 and 32 are also used in the conventional pulse inversion method.

Figure 4A:
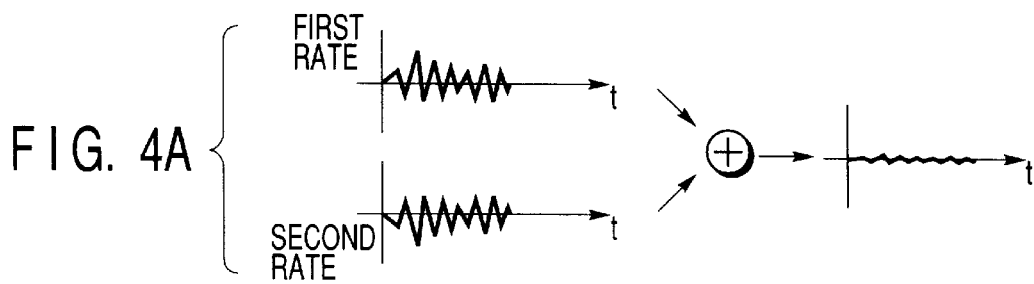
FIG. 4A is a graph showing how a fundamental wave is canceled by addition according to the pulse inversion method in this embodiment.
Figure 4B:
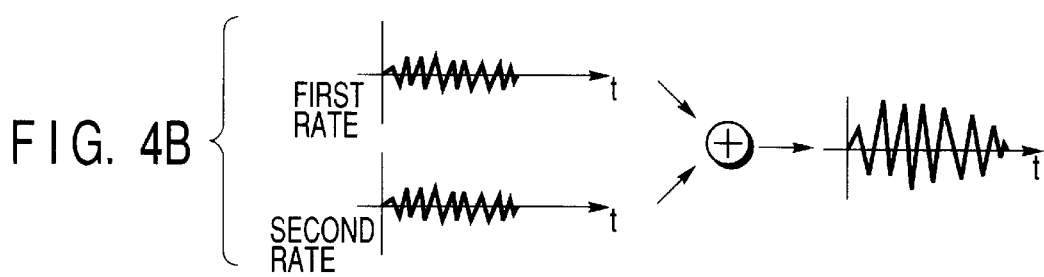
FIG. 4B is a graph showing how harmonic components is amplified by addition according to the pulse inversion method in this embodiment.
Figure 4C:
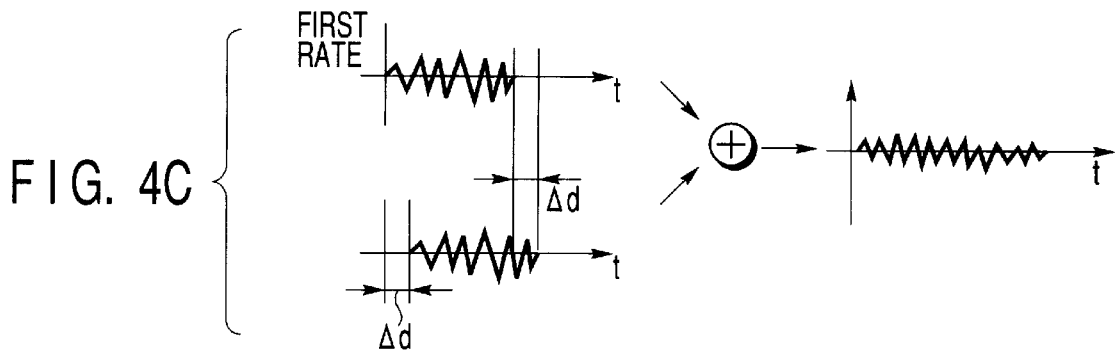
FIG. 4C is a graph showing a state where a fundamental wave is not canceled in the present of a tissue displacement in this embodiment.
Figure 4D:
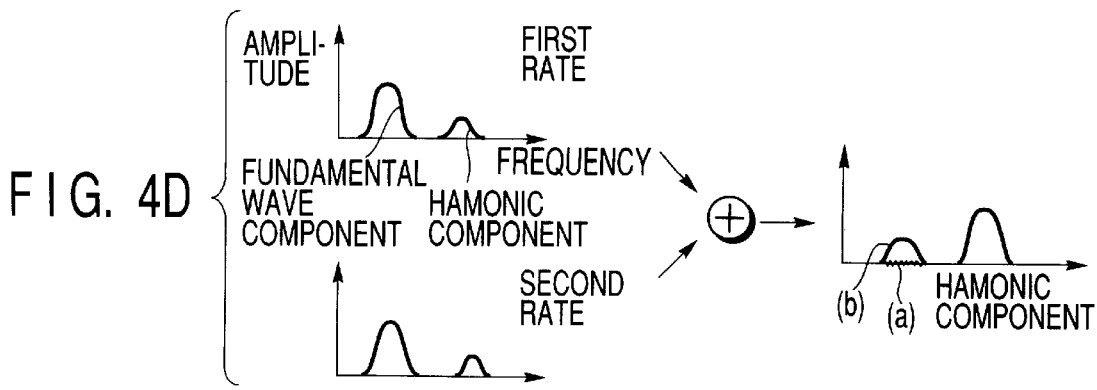
FIG. 4D is a graph showing extracted harmonic components in this embodiment.

FIGS. 4A to 4D show echo signals at a depth of interest, among received signals that have returned to the ultrasonic probe after the respective ultrasonic pulses 31 and 32 were transmitted into the living body at the respective rates, propagated nonlinearly, and were reflected by acoustic impedance boundaries in the tissue or backscattered by small scatterers. If the motion (displacement) of the living body in rate intervals at the depth of interest is zero or negligible, there is no displacement (motion) between the received signals at the two rates. That is, no motion artifact occurs. FIG. 4A shows examples of echo signals each consisting of only the real part of the complex data of a fundamental wave component contained in a received signal. FIG. 4D is a graph in a frequency space. In this case, if the two signals are added as in the prior art, the fundamental wave components are completely eliminated. FIG. 4B shows only the real parts of harmonic components, which are extracted by adding, and the resultant signal amplitude is enhanced twice.

When the heart is to be directly scanned or the liver or the like influenced by the movement of the heart is to be scanned, the tissue is displaced during a rate interval (the reciprocal of a pulse repeating frequency PRF). In this case, the two signals have the relationship shown in FIG. 4C. In this case, reference symbol $\Delta d$ denotes the displacement of an echo signal near the depth of interest. This displacement corresponds to a value twice the distance displaced by the tissue in the rate interval.

Even if these signals are simply added as in the prior art, the fundamental wave components are left as shown in FIG. 4C. In a frame or image portion in which the tissue moves, a fundamental wave component having a higher signal intensity than a harmonic component appears as a motion artifact, and it looks as if it were flashing on the image. According to an apex cordis approach, a motion artifact is noticeable at a basis cordis portion or cardiac apex portion which actively moves especially at the timing of systole or diastole.

(Elimination of Motion Artifact)

Figure 5:
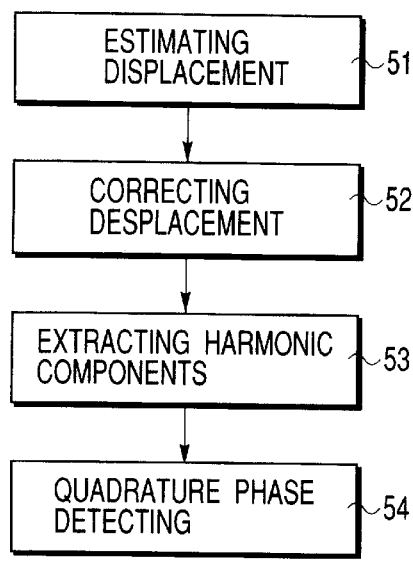
FIG. 5 is a flow chart showing a procedure for extracting harmonic components without any motion artifact in this embodiment.

A processing method for the extraction of harmonic components instead of motion artifacts, which is the gist of the present invention, will be described next. FIG. 5 is a flow chart showing a signal processing procedure in outline.

(Estimating Displacement 51)

First of all, the displacement estimating unit 19 measures (estimates) a relative displacement d at each depth between two rate signals. As will be described below, a plurality of methods are available as methods for this estimation, and any one of them can be used.

Figure 6:
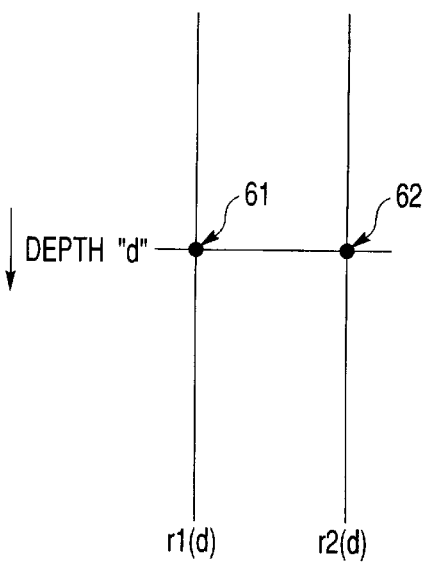
FIG. 6 is a view showing complex signals at the same depth between two rates in this embodiment.

According to the first method, as shown in FIG. 6, a complex value 61 of one rate signal at each depth d is multiplied by a complex conjugate value obtained by advancing the phase of a complex value 62 of the other rate signal at the corresponding depth by π (inverting a code consisting of only an imaginary number), and a phase argument θ of a multiplication result C. The reason why the phase is advanced by π is that these signals are received signals of pulses having opposite polarities.

A method of calculating a complex vector product by performing similar processing between a plurality of rates is an auto-correlation method. This case can be regarded as a special case of the auto-correction method, in which the number of data is two.

A displacement $\Delta dD$ can be obtained by normalizing the phase argument with $2\pi$ and calculating the product of the argument and the wavelength of a barycentric frequency component representing a fundamental wave component. The actual displacement in the living body is ½ the displacement obtained in this case. This is because a reflected signal is used as a received signal. Reference symbol A1 denotes the amplitude of a first rate received signal; A2, the amplitude of a second rate received signal, $\lambda$, the wavelength of a barycentric frequency component.

RATE 1 $\quad r_1(d) = A_1(d)e^{i\theta_1(d)}$

RATE 2 $\quad r_2(d)A_2(d)e^{i\theta_2(d)}$ $C(d) = A_1(d)e^{i\theta_1(d)} \times A_2(d)e^{-i(\theta_2(d)+\pi)}$ $\quad\quad = -A_1(d) \cdot A_2(d)e^{i\theta_1(d)-i\theta_2(d)}$ $\theta(d) = arg\{C(d)\}$ $\Delta d(d) = \dfrac{\theta}{2\pi} \cdot \lambda$ If a displacement is obtained after the calculated phase argument is spatially averaged near the depth of interest, variations due to noise and speckle can be reduced. If a spatial vector average is obtained with a complex vector before the acquisition of the phase argument, a probability average based on signal intensity can be obtained. This makes it possible to calculate a phase argument more accurately. This vector average is given by $$\overline{c(d)} = \frac{\sum_{N}^{N} r_1(d) \times (r_2^*(d))_{\theta \to \theta + \pi}}{N}$$

That is, cross-correlation operation with π=0 is equivalent to this.

Figure 7:
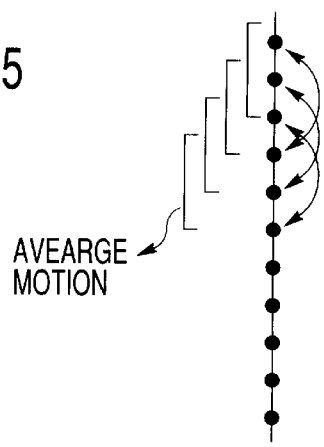
FIG. 7 is a view for a supplementary explanation of moving average processing in this embodiment.

As shown in FIG. 7, however, calculating a moving average after obtaining a complex vector at each point allows high-speed operation by interchanging the first and last values of data in moving operation.

As another method of obtaining phases, a method using cross spectra is available. However, this method is equivalent to the cross-correlation method, and hence a description thereof will be omitted.

In addition, spatial averaging may be performed across different scanning lines. After phases are calculated with scanning lines, the phases may be averaged across a plurality of scanning lines at the same depth. The barycentric frequency or the like of a fundamental wave component changes in the direction of depth owing to the influence of attenuation, a displacement may be calculated by using tables 81, 82, and 83 of the wavelengths of barycentric frequency components at different depths which are measured in advance. This makes it possible to accurately measure a displacement without measuring a barycentric frequency for every operation.

In the above method of obtaining phases, if a reflector or scatterer is displaced by ¼ the wavelength of a fundamental wave component between rates, aliasing occurs and a phase may not be accurately measured. In most organs, no problem arises because no tissue moves very fast. In circulatory organs, however, valves may present problems. A displacement that causes aliasing is determined by the wavelength of a frequency component of a fundamental wave component; a decrease in frequency will reduce the tendency to cause aliasing.

As shown in FIGS. 9A and 9B, if a phase is estimated from a signal as a low-frequency component extracted by filtering each rate signal, the precision improves, and the occurrence of aliasing can be prevented. If, for example, the speed of sound is 1,500 m/sec at a barycentric frequency of 3 MHz, the aliasing speed is 60 cm/sec. If, however, the barycentric frequency is decreased to 1.5 MHz by a filter or the like, the aliasing speed is doubled to 120 cm/sec.

The second method is a method of obtaining a displacement by a cross-correlation R near a depth of interest. As shown in FIG. 10, calculations are made while a cross-correlation coefficient between one signal with a length n near the depth and the other signal is relatively shifted so as to detect a shift width Δd with which the coefficient exhibits its peak. This value may be converted into a displacement. According to this calculation, calculations must be made after one of the codes is inverted owing to the polarity relationship between rates.

$$R(d, \Delta d) = \sum_{d-\frac{n}{2}}^{d+\frac{n}{2}} r_1(d) \times \{-r_2^*(d + \Delta d)\}$$

In general, it is easy to set a shift width in units of sampling intervals. However, a distance shorter than the sampling interval may be set as a shift width by interpolation.

The third method uses the least squares method, in which a add total E of values near the squares of the differences between one signal near the depth of interest and the other signal is calculated in the same manner as described above while one of the rate signals is shifted, as shown in FIG. 10, thereby obtaining a shift width exhibiting the minimum value as a displacement. As in the above case, owing to the polarity relationship between the rates, calculations must be made after one of the codes is inverted.

This operation can be expressed by the following equation; Δd that minimizes E may be found near the depth d.

$$E(d, \Delta d) = \Sigma |r_1(d) - \{-r_2(d + \Delta d)\}|^2$$

Since it is expected that much time is required for the cross-correction or least squares method, a technique of increasing the processing speed by, for example, thinning out signals or interpolating signals may be used. Method of thinning out signals include a method of thinning out signals at predetermined intervals and a method of making a calculation by using only components with strong signal intensity. In these methods, calculations may be performed for a plurality of scanning lines with respect to ultrasonic waves scanned three-dimensionally to three-dimensionally obtain a displacement, and the obtained displacement may be corrected. In addition, the relative positions of a pair of signals which are added by the pulse inversion method to be described later can also be obtained three-dimensionally.

The above displacement estimation is performed at each depth. For the sake of convenience, a table of displacements estimated in accordance with depths, like the table 83 in FIG. 8, may be formed in a memory to be looked up for correction.

(Technique 52 of Correcting Displacement)

A method of correcting the displacement obtained by "estimating displacement 51" by using the displacement correcting unit 20. Assume that in the first correcting method, two rate signals are stored in a memory, as shown in FIG. 11. The signal value of a signal 112, stored in the memory, which corresponds to a signal 111 at a given depth d is written in a new memory. This operation is performed at each depth, and signal processing may be performed by using the signal 111 and a signal 113 in the new memory.

In the second correcting method, as shown in FIG. 12, if the displacement calculated from cross-correlation operation using phases and interpolation is smaller than a sampling interval Δt, a displacement can be realized by interpolation. FIG. 13 shows an example of interpolation, which is realized by a sinc interpolation method of convoluting a rate signal to a sinc function, and data between sampling intervals is interpolated, thereby realizing a displacement. Obviously, this interpolation is not limited to "sinc". The interpolated signal may be written in a new memory 113.

As the third correcting method, a method of multiplying one signal by a phase term corresponding to the phase argument obtained above is available, although this is an approximation method.

The following are signal models of a received frequency component of a fundamental wave and its harmonic component before quadrature phase detection in a case where a reflector or scatterer is displaced by Δd between rate signals, and the displacement corresponds to T for each rate signal. Note that reference symbol F denotes the envelope of the fundamental wave component; and H, the envelope of the harmonic component.

$$T_{[\text{sec}]} = \frac{2 \cdot \Delta d [m]}{1500 [m/\text{sec}]} \quad t = \frac{2 \cdot d}{1500}$$

$$r_1(t) = F_1(t)e^{i(\omega t + \theta_1)} + H_2(t)e^{i(2\omega t + \theta_2)} \quad \text{RATE 1:}$$

$$r_2(t) = F_2(t)e^{i\{\omega(t-T)+\theta_1\}} + H_2(t)e^{i\{2\omega(t-T)+\theta_2\}} \quad \text{RATE 2:}$$

The phase estimated by the above method is a change amount ωT of the fundamental wave component. The phase change amount of the harmonic component is 2ωT. Even if, therefore, the phase term of ωT is multiplied as follows for correction, a phase difference corresponding to ωT remains in the harmonic component and becomes an error factor. Reference symbol r', denotes a received signal after correction.

$$r'_2(t) = r_2(t) \cdot e^{i\omega T}$$
$$= F_2(t)e^{i(\omega t + \theta_1)} + H_2(t)e^{i\{2\omega t - \omega T + \theta_2\}}$$

Figure 15A:
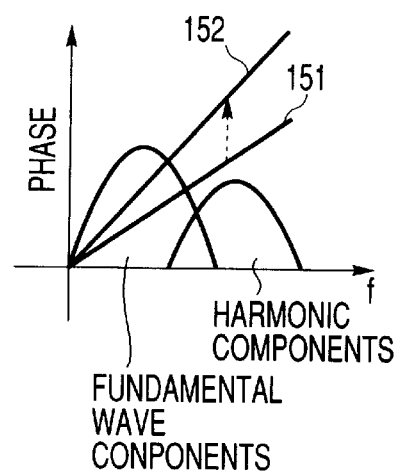
FIGS. 15A to 15C are graphs showing the difference between the displacement and product of phase terms on the frequency axis in this embodiment.
Figure 15B:
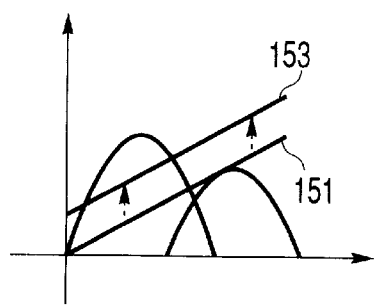
Figure 15C:
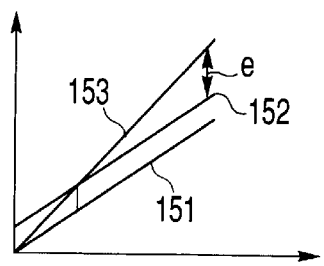

Consider operation on the frequency axis. Displacing a received signal near a given depth d amounts to changing, for example, a straight line 151, which represents the phase distribution of frequencies, to a straight line 152 in proportion to the frequency, as shown in FIG. 15A. In addition, as shown in FIG. 15B, multiplying a phase term is equivalent to adding/subtracting phases independent of frequencies like changing the straight line 151 to a straight line 153. When the processing results are overlaid as shown in FIG. 15C, a difference e obviously appears, which is an error factor. However, such an error can be neglected if the displacement is small, and hence a sufficient correcting effect can be expected even by such simple approximation processing.

Figure 16:
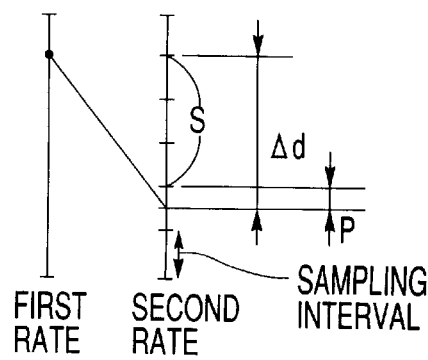
FIG. 16 is a view showing a displacement corresponding to a sampling interval unit and a displacement smaller than the unit.

As the fourth correcting method, a method of making a displacement in units of sampling intervals in a memory, and realizing the displacement amount obtained by subtracting the displacement from the original displacement by phase rotation may be used. Referring to FIG. 16, a displacement is made in the memory at a portion s, and a portion p is approximated by phase rotation. It can be expected that a displacement corresponding to the phase rotation amount used in this case is small with respect to the wavelength of a harmonic component as well. Therefore, sufficiently high precision can be expected. Obviously, correction can be performed with respect to any of the rates.

(Harmonic Extraction (Adding Processing) 53)

Figure 17:
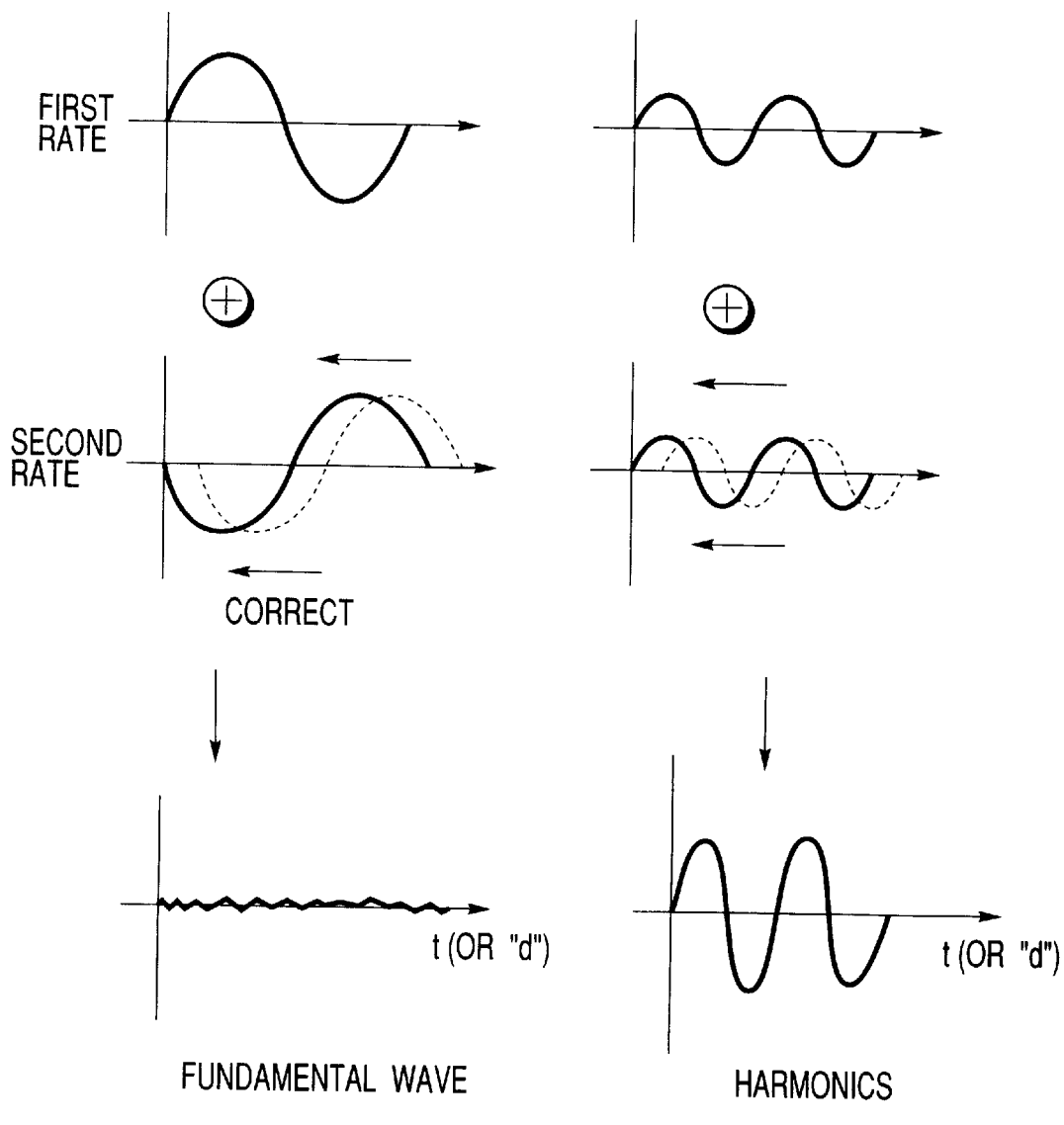
FIG. 17 is a graph showing the pulse inversion method in which displacement correction is performed in this embodiment.

By adding two signals having undergone displacement correction, fundamental wave components can be eliminated without any motion artifacts, and the harmonic components are amplified. FIG. 17 schematically shows a fundamental wave and harmonic component of a received signal from one reflector at a given depth in a case where a fundamental wave of a signal before phase detection can be expressed by a waveform corresponding to one period in "sin".

Figure 8:
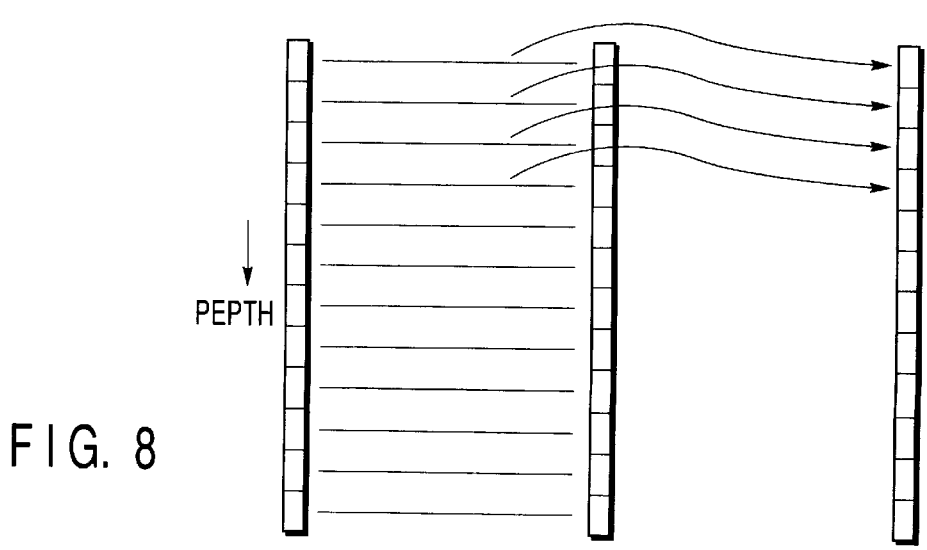
FIG. 8 is a view for a supplementary explanation of processing for the calculation of a displacement at each depth with the use of a wavelength table in this embodiment.
Figure 14:
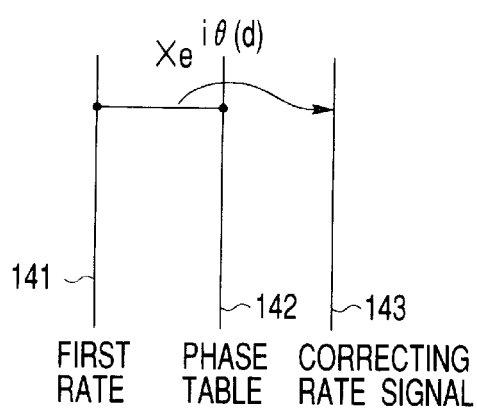
FIG. 14 is a supplementary explanation of processing of correcting a displacement by multiplying a complex value representing a phase term at each depth in this embodiment.

In adding operation, in correspondence with each depth of one rate signal, the corresponding depth value may be read out from the other rate signal by looking up the displacement table FIG. 8 instead of forming any new corrected memory as in the above case. In addition, adding can be performed after at least one signal is multiplied by a coefficient. By multiplying one signal by a positive number smaller than 1 and adding the resultant signals (multiplying different coefficients between rates and adding the resultant signals) at a near distance where a sufficient harmonic component is not produced or a deep portion where a harmonic component is greatly attenuated, a fundamental wave component remains and can be used for the generation of an image.

(Quadrature Phase Detection 54)

The adding result is stored in a memory for rate signals. Thereafter, to generate an image by using a harmonic component, quadrature phase detection is performed by quadrature phase detector 15 again by using the frequency of the harmonic component. The above processing is performed on all scanning lines necessary for the generation of a harmonic image under systematic management by a CPU 10. Thereafter, logarithmic compression, scanning/conversion, and the like are performed by the displaying unit 11 to display the resultant image on the monitor 3.

Figure 18A:
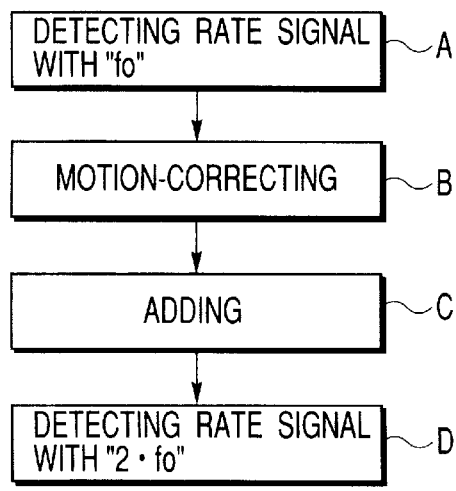
FIGS. 18A to 18C are flow charts showing variations of quadrature phase detection processing, motion correction processing, and addition processing in this embodiment.
Figure 18B:
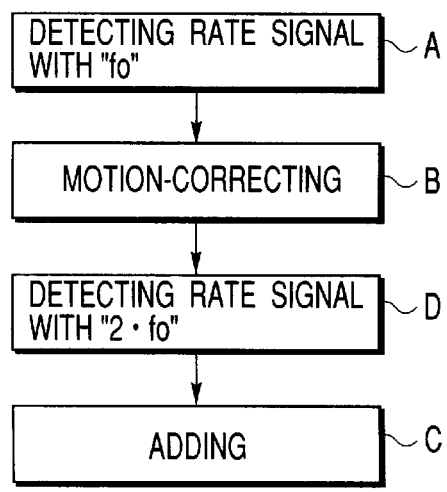
Figure 18C:
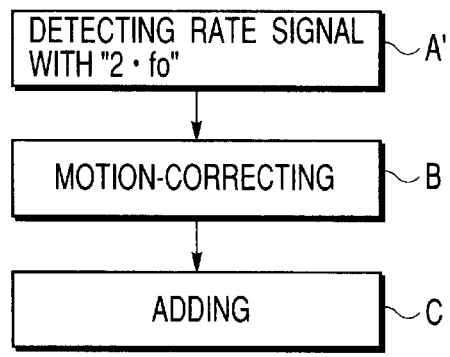
Figure 19:
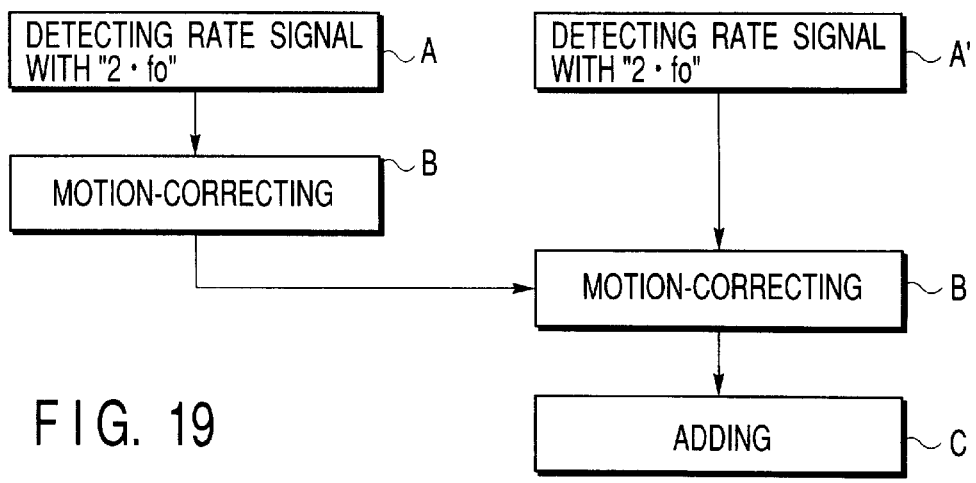
FIG. 19 is a flow chart showing variations of quadrature phase detection processing, motion correction processing, and addition processing in this embodiment.

The above processing is performed according to the procedure shown in FIG. 18A. However, adding (C) may be performed after quadrature phase detection (D), as shown in FIG. 18B. Alternatively, as shown in FIG. 18C, quadrature phase detection (A') may be performed first with a frequency twice a reference frequency f0. In addition, as shown in FIG. 19, a motion (displacement) may be estimated (E) on the basis of the result obtained by quadrature phase detection (A) with f0, and motion correcting (B) may be performed by using this displacement with respect to the result obtained by performing quadrature phase detection (A') with 2·f0.

The method of extracting a nonlinear component of tissue propagation at two rates while eliminating motion artifacts has been described above. However, the present invention can be effectively applied to a case where a nonlinear component is extracted from a contrast echo as well as the case of tissue propagation. If a nonlinear component is visualized by this method at the time of application of a contrast medium, a fundamental wave component can be eliminated without any motion artifacts, and both a contrast echo and a tissue harmonic component can be visualized.

A method of extracting a contrast echo by eliminating a tissue harmonic component without any motion artifacts according to this embodiment will be described next.

(Rate Difference)

As ultrasonic pulses at two rates, pulses having the same waveform are used. If there is no tissue motion, the displacement between the two rates at each depth is 0. FIGS. 20A and 20B show a combination of a fundamental wave component and tissue harmonic component of a signal at a given depth and a contrast medium harmonic component. By calculating the difference between these signals, the fundamental wave component and tissue harmonic component are canceled out, and only a change in the nonlinear response of microbubbles as a contrast medium between the rates over time is extracted. A change over time is caused by a change in scatterer distribution, e.g., a change in scattering intensity due to collapse, segmentation, and coagulation of bubbles, a change in diameter, and the like. As in the pulse inversion method, if there is a tissue motion, a displacement occurs between the reception rates at each depth, and the fundamental wave component and tissue harmonic component are not eliminated, as shown in FIG. 20C.

If a phase and displacement are estimated by the same method as in the case of pulse inversion and corrected and the resultant data is finally subjected to subtraction by the same method as described above, only a component corresponding to a change in contrast medium over time can be extracted. FIG. 21 shows how a displacement between a fundamental wave component and a tissue harmonic component in signals at two rates is corrected and eliminated.

(Problem Associated with Motion Artifact and Permanent Echo)

The above description has been made about a case where signal processing is performed by using two rates. As a method of detecting a displacement, a method of correcting a displacement, and a signal processing method, general methods can be used, and the present invention can be equally applied to a case where more signals are used. Motion artifact elimination based on addition/subtraction of pulses between the two rates described above is effective when a motion component of a fundamental wave echo contains only one type. That is, the effect of this method can be expected in eliminating motion artifacts due to, for example, heart beats in an abdominal region.

With regards to ultrasonic echoes from the heart, however, an echo from the moving heart tissue and a permanent echo such as a multiple echo at the pleurapophysis or an echo from the lung are often mixed in a received signal of a fundamental wave. Even if a displacement is estimated for such a received signal, both echoes may not be perfectly eliminated for the following reason. It is expected that displacement estimation will be greatly influenced by one of a permanent echo and a tissue echo which exhibits a higher signal intensity. Even if displacement correction and harmonic extraction are processed on the basis of this displacement estimation, one of the echoes may remain in amount that cannot be neglected for a harmonic component.

Figure 22:
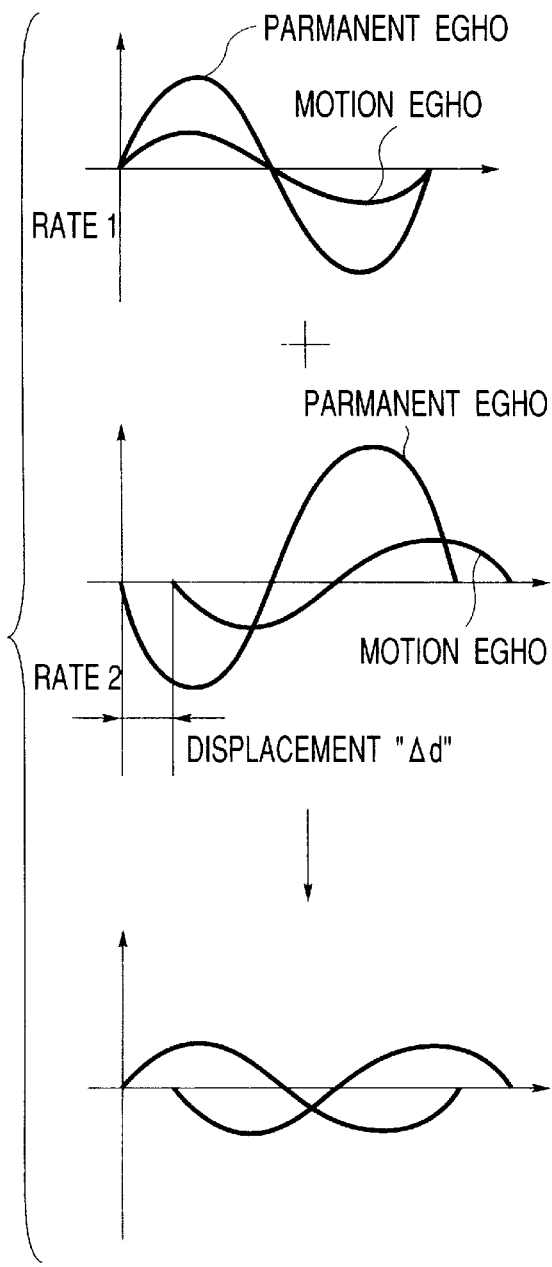
FIG. 22 is a graph showing the pulse inversion method in which displacement correction is performed when a permanent echo and motion echo from the tissue are present in this embodiment.

FIG. 22 schematically shows a fundamental wave component signal before quadrature phase detection. More specifically, FIG. 22 shows how a motion echo is left after the received signal is corrected with a displacement of 0 in accordance with a permanent echo having a high signal intensity.

Figure 23:
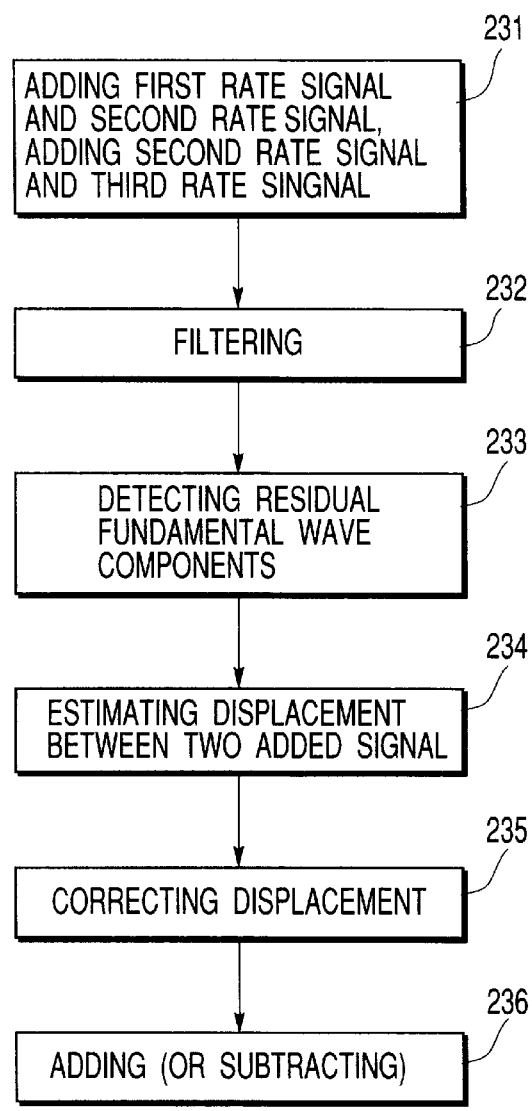
FIG. 23 is a flow chart showing a procedure for extracting harmonic components while eliminating permanent echoes and motion echoes by using three rates in this embodiment.

A method of eliminating both the moving tissue echo and permanent echo as fundamental wave components will be described with reference to the flow chart of FIG. 23.

(Third Rate Harmonic)

In transmitting operation, two types of ultrasonic pulses having opposite polarities are transmitted to each of a plurality of scanning lines three times, and the resultant signals are received. In this case, transmission/reception is performed in the order of positive polarity, negative polarity, and positive polarity. Obviously, however, this operation can be performed in the order of negative polarity, positive polarity, and negative polarity.

Figure 24A:
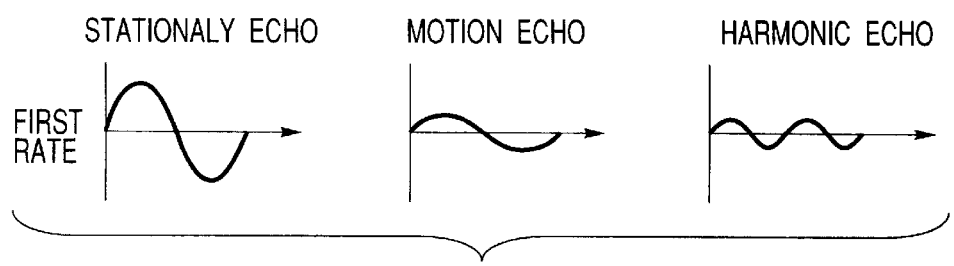
FIGS. 24A to 24C are graphs showing received signal components in the three-rate pulse inversion method in this embodiment.
Figure 24B:
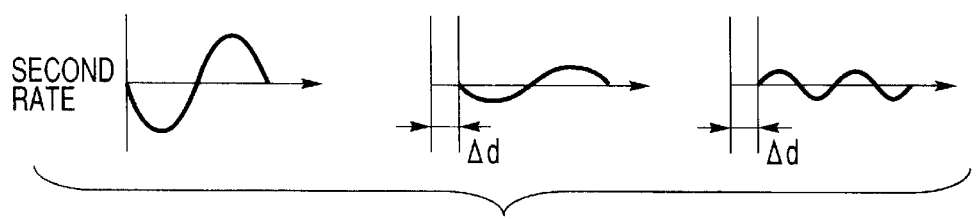
Figure 24C:
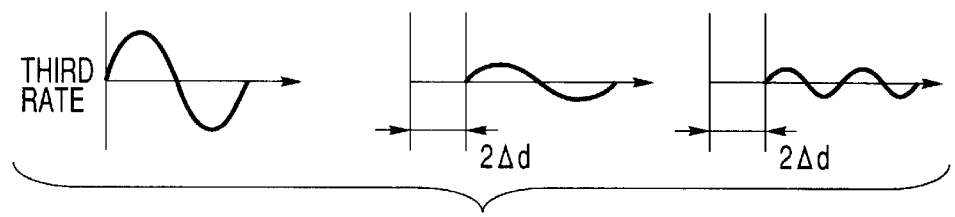

FIGS. 24A to 24C are graphs each showing a received signal at a given depth before quadrature phase detection, and more specifically, a motion echo, permanent echo, and tissue harmonic component, as fundamental wave components, separately. Note that "Re{A}" indicates the real part of A.

Figure 25A:
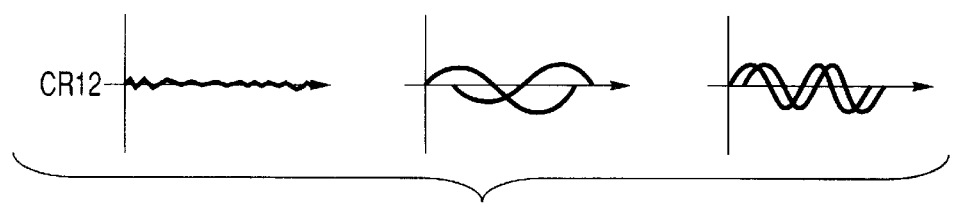
FIGS. 25A and 25B are graphs showing the signal components of an addition signal in this embodiment.
Figure 25B:
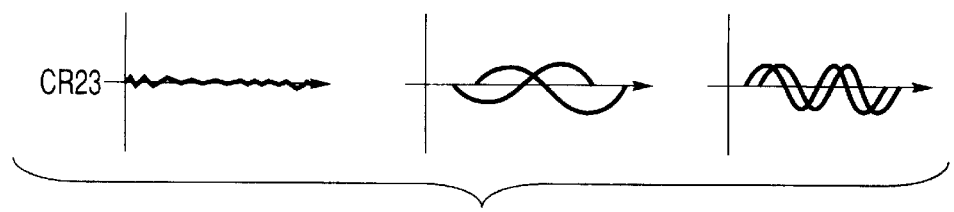

$r_1(t) = {}^{Re}\{Ae^{i\omega t} + Be^{i\omega t} + He^{i \cdot 2\omega t}\}$    RATE 1:

$r_2(t) = {}^{Re}\{-Ae^{i\omega t} - Be^{i\omega(t-T)} + He^{i \cdot 2\omega(t-T)}\}$    RATE 2:

$r_3(t) = {}^{Re}\{Ae^{i\omega t} + Be^{i\omega(t-2T)} + He^{i \cdot 2\omega(t-T)}\}$    RATE 3:

In step 231, a first rate received signal and second rate received signal are added to produce a new signal R12. Likewise, the second rate received signal and a third rate received signal are added to produce a new signal R23. That is, simple pulse inversion is performed twice. FIGS. 25A and 25B show the signals obtained by this addition, which are expressed by the following equations. Each of FIGS. 25A and 25B separately shows signal components before addition; the actual amplitude is the add of the amplitudes of these signal components.

$$R12(t) = r_1(t) + r_2(t)$$
$$= {}^{Re}\{Be^{i\omega t}(1 - e^{-(i\omega T + \pi)}) + He^{i \cdot 2\omega t}(1 - e^{i \cdot 2\omega T})\}$$

$$R23(t) = r_2(t) + r_3(t)$$
$$= {}^{Re}\{Be^{i(\omega t - T)}(1 + e^{-i(\omega T + \pi)}) + He^{i \cdot 2\omega(t-T)}(1 - e^{i \cdot 2\omega T})\}$$

Although the tissue echo component is left upon this operation, the permanent echo can be eliminated. Each of the signals R12 and R23 contains a tissue echo of a fundamental wave and a harmonic component.

In step 232, since both the fundamental wave component and the harmonic component may have the same signal level, filtering is performed to extract only the fundamental wave in order to improve the precision in measuring a phase with the fundamental wave in the following operation. FIG. 26 is a graph showing a change in frequency component accompanying addition in simple pulse inversion and how a harmonic component is eliminated by a filter.

In step 233, whether the tissue echo of the fundamental wave is sufficiently canceled by simple pulse inversion after filtering is determined for each sample point. At a sampling point where it is determined that a tissue echo is sufficiently canceled, the processing is stopped. That the tissue echo is sufficiently canceled indicates that the tissue echo is obtained from the tissue at rest and is canceled concurrently with the permanent echo. Therefore, there is no need to continue the processing.

Even if the following processing is continued in spite of sufficient cancellation of fundamental wave components, since the signal amplitude is small and the S/N ratio is low, the reliability of the result is low. As a criterion for determining whether fundamental wave components are sufficiently canceled, the power value of a signal is preferably used. A power value is calculated at each sampling point, and the calculated value is compared with a preset value. If the calculated value is smaller than the preset value, the processing may be interrupted. As this value, noise level or the like can be suitably used.

In step 234, a phase or displacement is detected at each depth with respect to the signals R12 and R23 and corrected as in the case of two rates.

In step 236, if addition is performed in the same manner as described above, a motion echo of a fundamental wave component is canceled. At this time, tissue harmonic components are added and extracted. FIG. 27 shows how signals are corrected and added. An extracted signal H123 can be expressed by $$H_{123} = R12(t) + R23(t + T)$$
$$= {}^{Re}\{4He^{i \cdot 2\omega t}(1 + e^{i \cdot 2\omega T})\}$$

In the above manner, after conventional pulse inversion is performed twice by using ultrasonic pulses at three rates whose polarities alternately change, displacement correction is performed, and the resultant signals are added. This makes it possible to extract a harmonic component while eliminating both a permanent echo contained in a fundamental wave component and a tissue echo that causes motion artifacts.

The above description has been made about a tissue harmonic component without any contrast medium. If the above method is applied to a contrast echo, both a tissue harmonic component and a nonlinear response component based on the contrast medium can be extracted. If a fundamental wave component contains both a permanent echo and a tissue motion echo, as in the case of two rates, a nonlinear component based on the contrast medium can be separated from a tissue harmonic component and extracted by the following processing.

(Three Rate Contrast Medium)

Figure 28A:
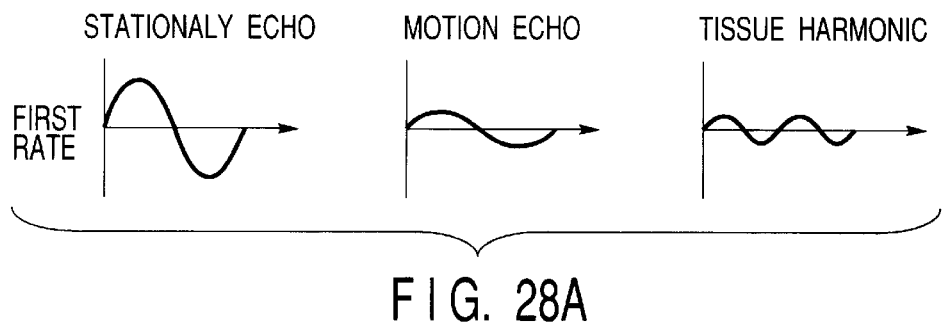
FIGS. 28A to 28C are graphs showing signal components based on rate differences in a three-rate difference method in this embodiment.
Figure 28B:
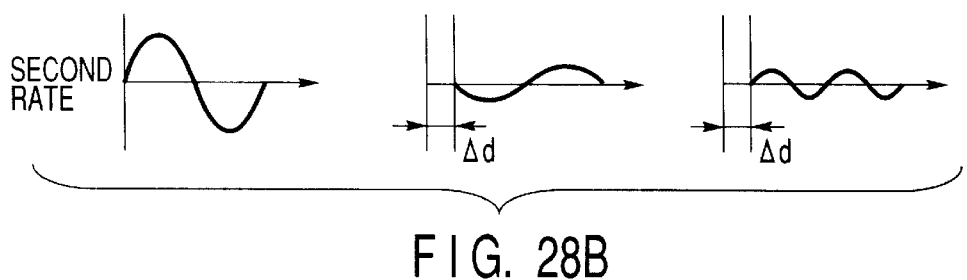
Figure 28C:
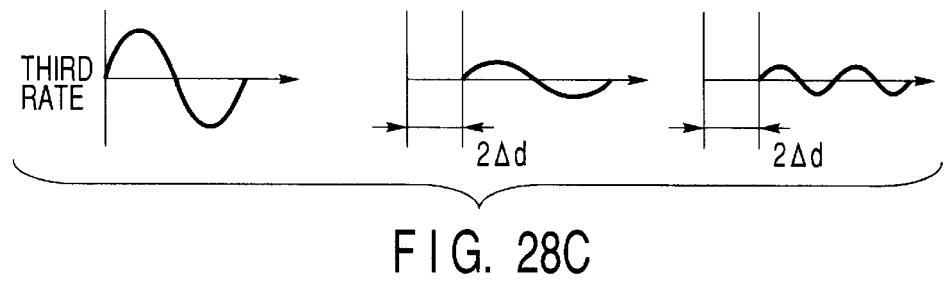

In transmitting operation, the same waveform is transmitted three times with respect to each of a plurality of scanning lines, and the resultant signals are received. Each of FIGS. 28A to 28C separately shows fundamental wave components of a received signal, i.e., a motion echo, permanent echo, and tissue harmonic component. Note that reference symbol A denotes the envelope of the permanent echo; B, the envelope of the motion echo; and C, the envelope of the harmonic component.

$$r_1(t) = {}^{Re}\{A(t)e^{i\omega t} + B(t)e^{i\omega t} + H(t)e^{i\cdot 2\omega t}\} + C_1 e^{i\cdot 2\omega t}$$

$$r_2(t) = {}^{Re}\{+Ae^{i\omega t} + Be^{i\omega(t-T)} + He^{i\cdot 2\omega(t-T)}\}C_2 e^{i\cdot 2\omega(t-T)}$$

$$r_2(t) = {}^{Re}\{Ae^{i\omega t} + Be^{i\omega(t-2T)} + He^{i\cdot 2\omega(t-2T)}\} + C_3 e^{i\cdot 2\omega(t-2T)}$$

Figure 29A:
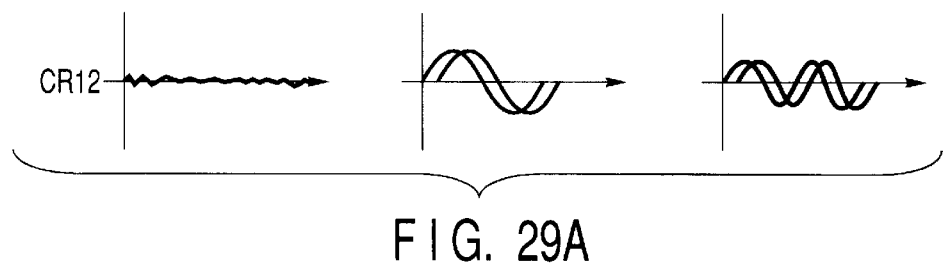
FIGS. 29A and 29B are graphs showing difference signal components in this embodiment.
Figure 29B:
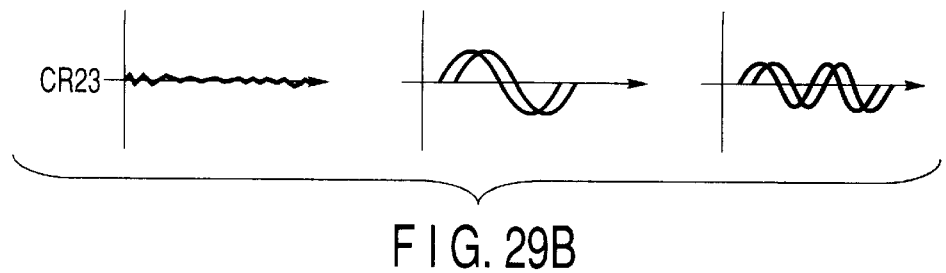

First of all, the first rate received signal and second rate received signal are subtracted from each other to produce a new signal CR12. The second rate received signal and third rate received signal are subtracted from each other to produce a signal CR23. That is, simple rate subtractions are performed. FIGS. 29A and 29B show the two signals obtained by the subtractions.

$$\begin{aligned} C^{R12(t)} &= r_{1(t)} + r_{2(t)} \\ &= {}^{Re}\{Be^{i\omega t}(1 - e^{-(\omega T + \pi)}) + \\ & He^{i\cdot 2\omega t}(1 - e^{i\cdot 2\omega T})\} {}^{+C_1^{(T)} e^{i\cdot 2\omega t}}_{-C_2(t)e^{i\cdot 2\omega}} \end{aligned}$$

$$\begin{aligned} C^{R23(t)} &= r_{2(t)} + r_{3(t)} \\ &= {}^{Re}\{+Be^{i(\omega t-T)}(1 - e^{-(\omega T + \pi)}) + \\ & He^{i\cdot 2\omega(t-T)}(1 - e^{i\cdot 2\omega T})\} {}^{+C_2(t)e^{i\cdot 2\omega}}_{-C_3(t)e^{i\cdot 2\omega}} \end{aligned}$$

Each of FIGS. 29A and 29B separately shows signal components before a subtraction; the actual amplitude is the difference between them. With this operation, although a tissue echo component that causes a motion artifact is left, a permanent echo can be eliminated. The signals CR12 and CR23 contain tissue echoes of the fundamental wave and harmonic components.

Figure 30:
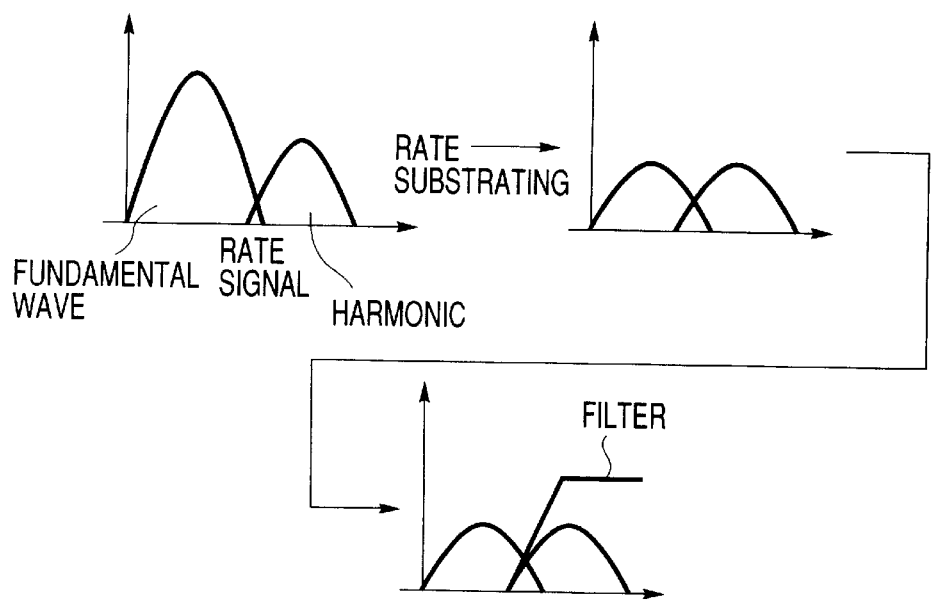
FIG. 30 is a graph for a supplementary explanation of filtering processing of eliminating harmonic components in this embodiment.

As shown in FIG. 30, after a simple rate subtraction, since both a fundamental wave and a harmonic component may have similar signal levels, filtering is performed to extract only the fundamental wave in order to improve the precision in measuring a phase with the fundamental wave.

After the filtering processing, whether the tissue echo of the fundamental wave is sufficiently canceled by one simple rate subtraction is determined for each sample point. At a sampling point where it is determined that a tissue echo is sufficiently canceled, the processing is stopped. That the tissue echo is sufficiently canceled indicates that the tissue echo is obtained from the tissue at rest and is canceled concurrently with the permanent echo.

In addition, at this time, a tissue harmonic component of the harmonic components is an echo at rest between rate intervals and canceled. only a change in nonlinear response of the contrast medium between the rates is a residual signal component, and hence only a nonlinear component based on bubbles is extracted.

Therefore, there is no need to continue the processing. Even if the following processing is continued in spite of sufficient cancellation of fundamental wave components, since the signal amplitude is small and the S/N ratio is low, the reliability of the result is low.

As a criterion for determining whether fundamental wave components are sufficiently canceled, the power value of a signal is preferably used. A power value is calculated at each sampling point, and the calculated value is compared with a preset value. If the calculated value is smaller than the preset value, the processing may be interrupted. As this value, noise level or the like can be suitably used.

Figure 31:
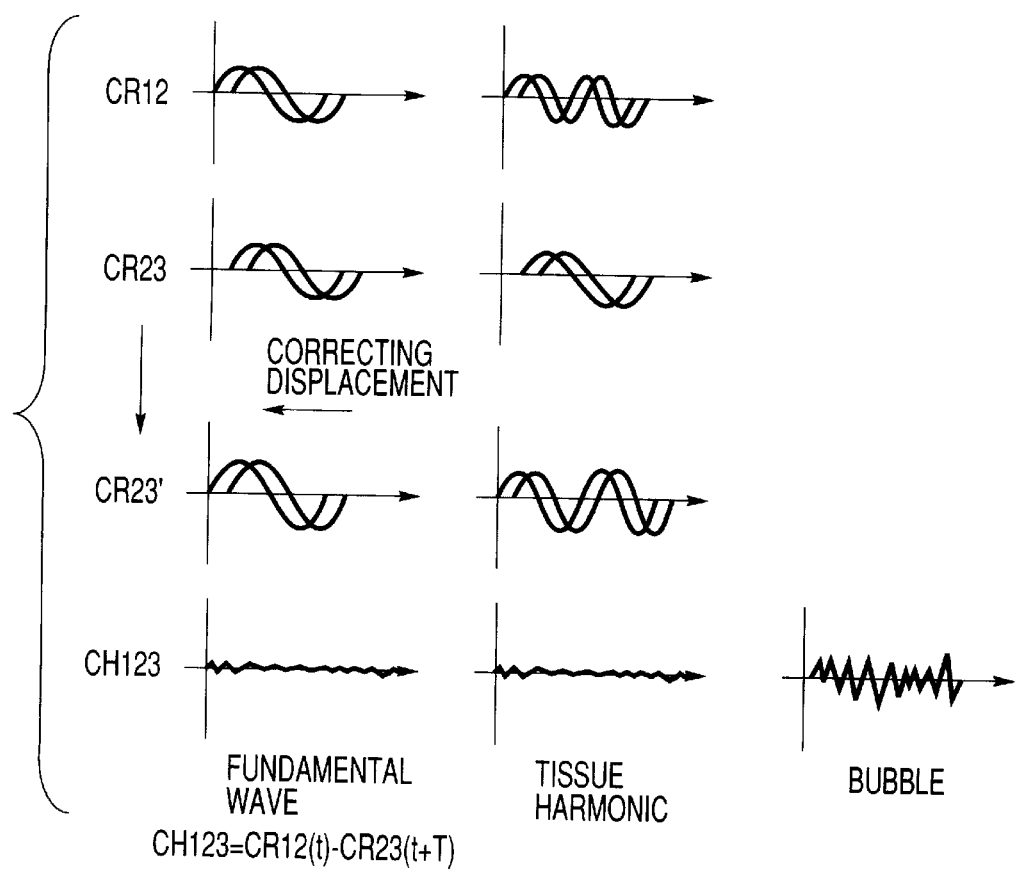
FIG. 31 is a graph for a supplementary explanation of processing of performing displacement correction for difference signals and further subtracting them from each other in this embodiment.

In steps 234 and 235, as in the case of two rates, a phase or displacement is detected and corrected at each depth. If a subtraction 236 is performed in the same manner, a motion echo of a fundamental wave component is canceled, together with a tissue harmonic component. In this case, only a component corresponding to a change in nonlinear response of the contrast medium over time between the rates is extracted. FIG. 31 shows how signal components are corrected and subtracted. An extracted signal CH123 can be expressed by the equation shown in FIG. 31.

As described above, after two conventional rate subtractions are performed by using ultrasonic pulses at three rates which have the same waveform, displacement correction is performed, and the resultant signals are subtracted from each other. This makes it possible to extract harmonic components based on the contrast medium while eliminating three components, i.e., a permanent echo contained in a fundamental wave component, a tissue echo that cases a motion artifact, and a tissue harmonic component.

In the above displacement detection and correction processing with two and three rates, an error that cannot be neglected may occur in detection and correction of a displacement due to system noise, a quantization error, or overlapping of an original echo and a multiple echo (from the heart and pleurapophysis/lungs). FIG. 32A is a graph showing fundamental wave components in a case where ultrasonic pulses which are alternately inverted are transmitted at a plurality of rates, and an error is caused in processing for echoes from a single scatterer. Even if the signals containing this error are simply added, the fundamental wave is left. To eliminate the influence of this error and prevent the fundamental wave from being left, signal processing may be performed after correction is performed and different coefficients are multiplied for the respective rates. That is, filtering may be performed in the rate direction (the time direction of data at the same position). In this case, the rate period becomes equal to the sampling period, and the reciprocal of the rate period becomes a sampling frequency f. With regard to fundamental wave components whose polarities are alternately inverted, if no error occurs, a phase rotates through π for each rate. If, therefore, frequency analysis is performed in the rate direction, a spectrum appears at f/2. A second harmonic component is distributed at zero as shown in FIG. 32B because the phase does not rotate. If an error occurs, second harmonic components are distributed near f/2 and zero, as shown in FIG. 32C. To extract the second harmonic component while eliminating fundamental wave components, a low-pass filter may be formed to eliminate the spectrum near f/2 and leave the spectrum near zero. Characteristics such as a cutoff characteristic of this filter may be designed in accordance with the occurrence state of an error. In addition, the filter coefficient may be changed at each depth. Although some rate may be cut upon filtering, the remaining rates may be used to generate an image. In addition, when the filter method is used, a fundamental wave can be eliminated with an odd number of rates unlike the conventional pulse inversion method. As described above in association with the second harmonic component and fundamental wave, of other harmonic components, some components are distributed at f/2, and the other components are distributed at zero. Secondary harmonic components are distributed at zero.

The present invention is not limited to the above embodiment and can be variously modified. For example, according to the above description, in the processing for the extraction of harmonic components according to the present invention, ultrasonic pulses at two and three rates are used. However, the present invention is not limited and can be practiced in various modifications. When a displacement is to be detected and corrected at each depth with four or more rates, displacements between all the adjacent rates may be detected and corrected, or an average displacement throughout all the rates may be detected and may be corrected at each rate. When a contrast medium is used, a displacement may not be accurately detected due to the influences of the contrast medium in which the first rate exists in the fundamental wave band and changes randomly. In this case, a displacement may be detected between the subsequent rates, and the first rate may be corrected by approximately using the detected value. Alternatively, displacements obtained between a plurality of rates may be simply averaged to reduce the influences of variations.

In addition, as a transmission ultrasonic wave, ultrasonic pulses that have been used in the prior art need not always be used. obviously, the above technique of correcting displacements between pulses is a general method and hence can be applied to any other signal processes using more rates. Furthermore, displacement correction need not always be performed between adjacent rates. Moreover, pulse inversion and rate subtraction may be combined.

Additional advantages and modifications will readily occur to those skilled in the art. Therefore, the invention in its broader aspects is not limited to the specific details and representative embodiments shown and described herein. Accordingly, various modifications may be made without departing from the spirit or scope of the general inventive concept as defined by the appended claims and their equivalents.

What is claimed is:

1. An ultrasonic diagnosis apparatus comprising:
   an ultrasonic probe;
   a transmitter configured to supply a transmission pulse to said ultrasonic probe to repeatedly transmit an ultrasonic wave to each of a plurality of scanning lines;
   a receiver configured to receive echoes of the ultrasonic waves through said ultrasonic probe and obtaining a plurality of received signals for each of the plurality of scanning lines;
   a displacement estimating means configured to estimate a relative change accompanying a tissue motion between a plurality of received signals associated with each of the plurality of scanning lines;
   a displacement correcting means configured to correct the plurality of received signals in accordance with the change detected by the displacement estimating means;
   a harmonic component extracting means configured to extract a harmonic component from the plurality of received signals corrected by said displacement correcting means;
   a display means configured to generate an ultrasonic image on the basis of the harmonic component extracted by said harmonic component extracting means; and
   a monitor configured to display the image generated by said display means.

2. An apparatus according to claim 1, wherein the change is calculated from a phase difference between the plurality of received signals.

3. An apparatus according to claim 1, wherein
   said transmitter transmits two ultrasonic pulses whose polarities are substantially inverted from each other to each of the plurality of scanning lines,
   said receiver receives echoes of the two ultrasonic pulses and acquires two received signals for each of the plurality of scanning lines,
   said displacement estimating means detects at least one of a relative displacement and phase difference for each portion between received signals,
   the displacement correcting means corrects at least one of the displacement and phase difference for each portion between the received signals;
   said harmonic component extracting means adds the corrected signals,
   said display means generates an image from the signal obtained by addition, and
   said monitor displays the generated image.

4. An apparatus according to claim 3, wherein the phase is detected by at least one of an auto-correlation method, cross-correlation method, cross spectrum, and complex conjugate product.

5. An apparatus according to claim 3, wherein the displacement is detected by at least one of a cross-correlation method and least squares method.

6. An apparatus according to claim 3, wherein said displacement correcting means corrects the received signal in means of sampling intervals on the basis of the displacement detected by said displacement estimating means, and performs correction in an interval smaller than the sampling interval in accordance with a phase.

7. An apparatus according to claim 1, wherein
   said transmitter transmits two ultrasonic pulses having substantially the same waveform to each of the plurality of scanning lines,
   said receiver receives echoes of the two ultrasonic pulses and acquires two received signals for each of the plurality of scanning lines,
   said displacement estimating means detects at least one of a relative displacement and phase difference for each portion between received signals,
   the displacement correcting means corrects at least one of the displacement and phase difference for each portion between the received signals;
   said harmonic component extracting means subtracts the corrected signals from each other;
   said display means generates an image from the signal obtained by subtraction, and
   said monitor displays the generated image.

8. An apparatus according to claim 1, wherein signal processing by said harmonic component extracting means, detection of a relative change by said displacement estimating means, and correction by said displacement correcting means are repeated a plurality of times in an arbitrary order.

9. An apparatus according to claim 5, wherein the displacement is obtained from a product of the phase and a wavelength corresponding to a frequency contained in an ultrasonic wave transmitted by said transmitter.

10. An apparatus according to claim 5, wherein said displacement estimating means comprises filter means configured to filter the received signal and a means configured to obtain the phase from the filtered received signal.

11. An apparatus according to claim 5, wherein after the correction, signal processing is performed upon multiplication of each rate by a coefficient corresponding to a depth.

12. An apparatus according to claim 5, wherein after the correction, signal processing of eliminating a fundamental wave component is performed upon multiplication of each rate by a coefficient corresponding to a depth.

13. An apparatus according to claim 5, wherein the coefficient is set to form a filter in a rate direction.

14. An apparatus according to claim 5, wherein in the detection and correction, displacements are detected at portions corresponding to a plurality of rates, an average displacement is calculated, and correction is performed on the basis of the displacement.

15. An apparatus according to claim 5, wherein in the detection and correction, displacements are detected between a plurality of rates, an average displacement is calculated, and correction is performed on the basis of the displacement.

16. An apparatus according to claim 15, wherein the correction is not performed when variations in displacement detected between a plurality of rates are large.

17. An apparatus according to claim 1, wherein said transmitter transmits three ultrasonic pulses formed by two types of waveforms whose polarities are substantially inverted from each other to each of the plurality of scanning lines, said receiver receives echoes of the three ultrasonic pulses and acquires three received signals for each of the plurality of scanning lines, said harmonic component extracting means generates a first addition signal by adding a first rate received signal and second rate received signal, and generates a second addition signal by adding the second rate received signal and third rate received signal, said displacement estimating means detects at least one of a relative displacement and phase difference at each portion between the first addition signal and second addition signal, said displacement correcting means corrects at least one of the displacement and phase difference at each portion of the signal, and said signal processing means adds the corrected signals, said display means generates an image from the signal obtained by addition, and said monitor displays the generated image.

18. An apparatus according to claim 17, further comprising a filter configured to perform filtering processing to eliminate a harmonic component of an ultrasonic wave transmitted by said transmitter before detection of the phase difference.

19. An apparatus according to claim 17, further comprising a detecting means configured to detect a residual fundamental wave component on the basis of a power value or amplitude of a signal of a fundamental wave component after processing performed by said harmonic component extracting means.

20. An apparatus according to claim 19, wherein if a fundamental wave component detected by said displacement estimating means is smaller than a set threshold, signal processing is terminated in accordance with each depth of a rate signal.

21. An apparatus according to claim 20, wherein the threshold is a noise level corresponding to a depth.

22. An apparatus according to claim 1, wherein said transmitter transmits three ultrasonic pulses having substantially the same waveform to each of the plurality of scanning lines, said receiver receives echoes of the three ultrasonic pulses and acquires three received signals for each of the plurality of scanning lines, said harmonic component extracting means generates a first subtraction signal by adding or subtracting a first rate received signal and second rate received signal from each other, and generates a second subtraction signal by adding or subtracting the second rate received signal and third rate received signal from each other, said displacement estimating means detects at least one of a relative displacement and phase difference at each portion between the first subtraction signal and second subtraction signal, said displacement correcting means corrects at least one of the displacement and phase difference at each portion of the signal, said harmonic component extracting means subtracts the corrected signals from each other, said display means generates an image from the signal obtained by subtraction, and said monitor displays the generated image.

23. An apparatus according to claim 18, further comprising a filter configured to perform filtering processing to eliminate a harmonic component of an ultrasonic wave transmitted by said transmitter before detection of the phase difference.

24. An apparatus according to claim 18, further comprising a detecting means configured to detect a residual fundamental wave component on the basis of a power value or amplitude of a signal of a fundamental wave component after processing performed by said harmonic component extracting means.

* * * * *